United States Patent
Pyntikov et al.

(10) Patent No.: US 6,960,451 B2
(45) Date of Patent: Nov. 1, 2005

(54) PROTEOLYTIC FERMENTER

(75) Inventors: Alexander V. Pyntikov, Ashburn, VA (US); Salvatore P. Salerno, Herndon, VA (US)

(73) Assignee: Green Earth Industries, Sterling, VA (US)

( * ) Notice: Subject to any disclaimer, the term of this patent is extended or adjusted under 35 U.S.C. 154(b) by 0 days.

(21) Appl. No.: 10/358,137

(22) Filed: Feb. 5, 2003

(65) Prior Publication Data

US 2003/0148418 A1 Aug. 7, 2003

Related U.S. Application Data

(60) Provisional application No. 60/354,270, filed on Feb. 6, 2002.

(51) Int. Cl.⁷ ................................................ C12P 21/06
(52) U.S. Cl. ..................................................... 435/68.1
(58) Field of Search ......................................... 435/68.1

(56) References Cited

U.S. PATENT DOCUMENTS 4,443,540 A    4/1984   Chervan et al.
5,053,234 A   10/1991   Anderson et al.

FOREIGN PATENT DOCUMENTS

| RU | 2020153 | 9/1994 |
| RU | 2068879 | 11/1996 |
| RU | 2074249 | 2/1997 |
| RU | 2103360 | 1/1998 |
| WO | WO 89/10960 | 11/1989 |
| WO | WO 99/29836 | 6/1999 |
| WO | 01/28353 A1 | 4/2001 |

*Primary Examiner*—Herbert J. Lilling
(74) *Attorney, Agent, or Firm*—Heller Ehram White and McAuliffe LLP (57) ABSTRACT

A process of controlling the production of enzymatic protein hydrolysate from cold water animals, containing up to 90% free amino acids, cold fish oil, hydroxilaptite (calcium orthophosphate), proteins, peptides, vitamin, minerals and calcium salts of phosphorus. The process provides a greater degree of refining than existing technology through the use of acid and alkaline denaturation steps, in combination with advanced separation and drying technology. The new drying technology results in a higher-quality, less expensive mixture than was previously possible.

15 Claims, 8 Drawing Sheets

PROTEOLYTIC FERMENTER

RELATED U.S. APPLICATION DATA

This application claims the benefit of provisional application Ser. No. 60/354,270 entitled Proteol[ytic] Fermenter And Complex Technologies Using The Proteol[ytic] Fermenter, filed Feb. 6, 2002.

BACKGROUND OF THE INVENTION

1. Field of the Invention

The present invention relates to an industrial process for enzymatically hydrolizing marine animal biomass, products deriving therefrom, and a method of computer control for the process.

2. Background

In nature there are only a few basic models of terrestrial life; in biology we call them "kingdoms," and they include: prokaryotes, protests, fungi, plants and animals. The elementary nutrients for cellular growth of life on Earth are amino acids. Every chemical structure in all living organisms (DNA, RNA, proteins, fats, carbohydrates, hormones, vitamins, and the amino acids themselves) are synthesized and broken down by means of enzymes that, in turn, are proteins, constructed from amino acids. For representatives of all the five kingdoms of living organisms, life on Earth essentially is the circulation of amino acids. For example, representatives of the kingdom of plants continuously make contributions of mass doses of amino acids to global amino acid quantities (by way of photosynthesis).

Food is digested in the human body into amino acids, simple sugars and fatty acids. Amino acids are not only food for human beings, they are also a base for the rapid accumulation of biomass of individual species of organisms in any of the five kingdoms of the terrestrial life. Humans can help protect their species against vagaries and catastrophes within any of the kingdoms of living things on Earth by creating a steadily renewable supply of amino acids. Humans can use this resource to benefit a particular kingdom (for the production of meat, for example, or gas, or alcohol, or for the purification of water or air, or for combating the greenhouse effect on Earth.

Currently, abundant, inexpensive sources of mixtures of amino acids are not readily available. Existing commercial and previously patented processes make use of conventional spray dryer and crystallization technologies to produce amino acid in powder form. These technologies suffer from the following disadvantages. They require steam that adds substantial costs of production. They often require the use of special additives to enhance nucleation, which adds to the cost of making a final powder product. The temperature ranges over which they operate cause thermal damage to a significant portion of the final products due to hot spots and poor mixing within the drying chamber.

Another disadvantage of existing production methods is that they typically use only one denaturation step, either acid or alkaline. As a consequence of this approach, much of the amino acid powder that is produced has not been refined or purified to the greatest degree possible.

Related Definitions

PROTEINS: Proteins are high molecular weight organic compounds with molecular weights ranging from 5000 to many millions of daltons. Proteins are polymers (or copolymers), the monomers of which are amino acids connected to each other by peptide bonds. Peptide chains of smaller sizes (less than 5000 daltons) form peptide and polypeptide molecules. There are various principles for the classification of proteins based on composition, properties, where they are found in nature, and the functions they perform. With respect to composition, proteins are classified as simple or complex (proteins and proteids, or conjugated proteins). The composition of proteins includes, in addition to amino acids, components such as carbohydrates (glycoproteins), nucleic acids (nucleoproteins), fats (lipoproteins), phosphoric acid (phosphoproteins), metals (metalloproteins) or other compounds. One of the criteria used for classification is the solubility of the proteins in various solvents. Albumin and globulin, which dissolve in water and in weak aqueous solutions of electrolytes, are considered soluble proteins, although their stability in solution varies. At the opposite extreme are collagen and keratin—proteins which are insoluble in water and other solvents. In interaction with water, many of the insoluble proteins swell and form a gel (gelatinize). An additional criterion for classification is behavior in an electrical field, depending upon the total electrical charge of their molecules, which are polyions. The electrophoretic mobility of a protein at a specific pH level depends upon its amino acid composition and its isoelectric point (pI—the pH value of the medium at which the protein is electrically neutral). Basic, neutral and acidic proteins are distinguished according to their electrochemical properties. According to biological functions, proteins are classified as biologically active (enzymes, hormones), structural, regulatory, contractile, reserve, ovalbumin and casein type, transport (blood serum proteins, hemoglobin, myoglobin), protective (antibodies, blood coagulating proteins) and toxins. The whole spectrum of proteins is provided by the particular features of their structures. The protein part of the protein molecule is a polymer chain of amino acids connected by peptide bonds. Amino acids and peptides are formed in the hydrolysis of proteins.

AMINO ACIDS: Amino acids are optically active organic compounds containing an amino group and a carboxyl group at the carbon atom. In the condensation of two amino acids, the amino group of one of them enters into a linkage with the carboxyl group of the other. The linear sequence of amino acids in the polypeptide chain is considered the primary structure of the protein. Proteins are long-chain molecules that are intricately folded into 3-dimensional structures. The chain is composed of strings of small and fairly simple molecules called amino acids. The instructions for making proteins are carried by the DNA. In the 1960s the code for translating DNA sequences into protein structures was discovered, following intensive work since Watson and Crick's discovery of the double helical structure of the DNA molecule in 1953. The compositions of proteins include the 26 amino acids which are most common in nature in the stereo-isomeric form of L-isomers, and more than 10 rare and very rare amino acids. Out of the whole list, there are 8 amino acids that are essential; i.e., they cannot be synthesized in the bodies of animals and have to be obtained exclusively from their diet. Two amino acids are provisionally essential. The other amino acids can be synthesized in animal and plant organisms PEPTIDES: Proteins are synthesized as a result of the formation of secondary amide bonds between carboxyl groups and amino groups of adjacent amino acids. Such bonds are called peptide bonds, and the structures which emerge as a result of the formation of the peptide bonds between amino acid radicals are called peptides. A peptide that contains two amino acid radicals is called a dipeptide;

a peptide that contains three radicals is called a tripeptide, etc. The covalent peptide bonds and disulfide bonds with an energy greater than 35 kcal/mol are the most important bonds in the polypeptide chain. The peptide bonds [(C—N)-group] are partly double bonds and preclude the free rotation of the atoms. Since there is one peptide bond for every 3 bonds in the peptide chain, the free rotation is possible only around the other two bonds. As a result, the peptide chain is spontaneously twisted into a helix. The form of the spiral determines the nature of the secondary structure of the protein. Hydrogen bonds with an energy of 5 kcal/mol play a large role in the formation of the secondary structure. The method for the folding of the structure into its tertiary form is determined by weak interactions within the protein molecule: Coulomb (electrostatic) and Van der Waals. These bonds are very unstable under heating and, like hydrogen bonds, have a pronounced thermolabile nature. Nevertheless, all the other levels of structural organization and, consequently, the method of self-assembly of the molecules are programmed, as it were, in the amino acid sequences of the proteins. The accessibility of the peptide bonds to enzymes is of importance for the process of enzymatic hydrolysis. However, these bonds are normally masked inside a globule and are attached by hydrogen bonds to the neutral polar groups or form ion pairs. The denaturation of proteins results in unmasking of the susceptible bonds and opens them up to enzyme attack.

There are adequate industrial raw material sources of protein in all the industrially developed countries of the world. Protein sources may include wastes from the meat processing, fish processing and milk processing industries, vegetable proteins, as well as biomass from artificially cultivated microorganisms, fungi or one-celled algae. The criterion for the selection of proteins for hydrolysis is the nutritional value and completeness of the proteins in question. The nutritional value of proteins is determined at present by the calculation (scoring) method on the basis of the concentrations of essential amino acids. Essential amino acids pass into the human body and the bodies of animals with their diet, while bacterial and cell cultures receive them from the nutrient medium. The completeness of the proteins for nutritional purposes is determined by comparison to a protein that has been adopted as a standard. The calculation of the score consists of the quantitative determination of essential amino acids in the protein and the determination of the ratio of the concentration of each to the corresponding concentration in a standard specimen or model mixture. The value of the minimum ratio, i.e., the ratio for the limiting amino acid, is accepted as the score. Proteins from hen's eggs, mother's milk and goose eggs have been adopted as standard proteins. The process for the calculation of corrected amino acid scoring of protein compositions—i.e., the calculation of the score with correction for the susceptibility to breaking down (hydrolysis) of the protein—has been accepted since 1993.

Muscle tissue is a source of proteins which are the most balanced in regard to their amino acid composition, as well as mineral elements, vitamins and growth factors, including substances of a nature which is not yet known. Most biotechnologists have believed and continue to believe that meat cannot be replaced as a source of protein for nutrient media. At the same time, meat is one of the main food products. Therefore, meat is used extremely rarely as a source of raw material in the industrial production of hydrolysates, and it is used as efficiently as possible.

HYDROLYSIS: The hydrolysis of proteins is the splitting of the molecule with the destruction of its primary structure (the polypeptide chain). The hydrolysis of the peptide chain is the reverse of the process of formation of the peptide chain; it occurs as a result of the effects of physical factors (temperature, pressure), chemical reagents (acids, bases) or proteolytic enzymes. As a result of the hydrolysis of a dipeptide, two amino acid molecules are formed, and one molecule of water is absorbed: R—CHNH2—CO—NH—R—COOH+H—OH>R—CHNH2—COOH+NH2—R—COOH. The products of the full hydrolysis of proteins are amino acids; the products of partial hydrolysis are amino acids and peptides. Typically it is chemical or enzymatic methods that are used for hydrolysis. The chemical methods are used for full (total) hydrolysis of proteins and for partial hydrolysis and are also used in certain cases for the spot (selective) breaking of peptide bonds. The methods of full hydrolysis are used, as a rule, for purposes of analysis. Acid hydrolysis is used often under industrial conditions; alkali hydrolysis is more rarely used.

ACID HYDROLYSIS is conducted primarily with the use of mineral acids at high temperatures (acid-thermal hydrolysis). With the effect of high concentrations of the acids on the protein under heating for a sufficiently long period of time, the protein can be broken down completely into amino acids. Acid hydrolysis is normally performed with sulfuric or hydrochloric acid. An attractive aspect of acid hydrolysis is the possibility of obtaining deep hydrolysates in short periods of time. Another positive factor is the establishment of bactericide conditions in the course of the process, which prevents bacterial growth and makes it possible to store the hydrolysate for a long time without neutralization. However, acid hydrolysis also has its negative aspects. Since acid hydrolysis is not specific to proteins, in the acid-thermal treatment of a complex, mixed raw material of the kind normally used in industry, the breaking down of other biological polymers is also going on at the same time: nucleic acids and polysacharrides. As a result of the hydrolysis of such raw material, the hydrolysis products turn out to be not just amino acids and peptides but carbohydrates (monoses and reducing disacharrides). In acid hydrolysis, melanoids are formed—dark-colored, high molecular weight compounds with a tendency toward aggregation, which have poor solubility in water. The melanoids are cell toxins; therefore, their formation in the hydrolysate sharply reduces its quality. The neutralization of acids in the hydrolysate involves the formation of high concentrations of salts. The higher the concentration of the acid used for hydrolysis, the more salts are formed as a result of neutralization. The increased anion concentration is also a salient factor in the toxicity of the hydrolysate.

ALKALI HYDROLYSIS: In the alkali hydrolysis of proteins, most amino acids are broken down and more importantly, the method for alkali hydrolysis is softer and gentler than acid hydrolysis. As a result, alkali hydrolysis is best used in the industrial production of hydrolysates. Of the known means to hydrolyze proteins, enzymatic hydrolysis in a slightly alkaline environment at a moderate temperature, is preferred since these conditions do not significantly destroy essential amino acids. However, in the hydrolysis of animal biomass, most animal-produced enzymes, or ferments, are not robust enough to hydrolyze animal proteins under such mild conditions. Hydrolysis occurs in pH ranges that correspond to the peaks in the activity of the enzymes: more often in a neutral, slightly alkaline medium. The optimum temperature is 35–50° C. This threshold can be raised to 60° C. for certain enzymes, but should not be higher than 80° C. Despite its relative advantages, enzymatic hydrolysis of proteins—using natural ferments—has typically resulted in products whose constituents cannot be accurately predicted on a consistent basis. Further difficulties in industrial scale enzymatic hydrolysis of animal proteins using natural ferments stems from the fact that cost-effective industrial dryer and micro-separation technologies have not been utilized for the production of contaminant-free high-grade amino acids in this environment.

SUMMARY OF THE INVENTION

The present invention, enzymatic protein hydrolysis of marine animal biomass and methods for large-scale production of an enzymatic protein hydrolysate ("EPH," hereinafter) mixture comprising peptides, amino acids, vitamins, minerals, and specified elements. The production process involves mixing ground fish waste products with an enzyme source comprising cold-water fish guts and entrails—containing relatively aggressive enzymes—effective in a mild, slightly alkaline, medium of water. Such effectiveness is a function of the fact that fish are abundant; they are uniformly carnivorous, and in particular, cold-water fish have natural enzymes enabling them to digest proteins under conditions of relatively cold temperature ranges.

Enzymatic digestion of proteins takes place under continuous mixing and precisely controlled conditions until amino acids and very short peptides are produced. The enzymatic protein hydrolysate of the present invention is sterilized, and fish-oil and solid particles are removed by means of centrifuging. The EPH may be dried to a powder state. Fish-oil, vitamins, minerals, and solid particles are independent products of the given production process. The proposed production process is fully waste-free and nature-saving. EPH may be applied as an enhancer for the acceleration of known biological and industrial processes, and most particularly, processes depending upon bacterial or cellular action.

Our proteolytic fermenter may be utilized more effectively if the input material consists of bodies of marine animals (or parts of the waste produced by their bodies). Before input, the bodies must be broken up and reduced to a homogeneous mass. Then, as the mass is input into the machine and the appropriate chemical and physical conditions are reached, the proteins are deconstructed. Their deconstruction is aided by their own proteolytic ferments. These ferments are contained in the intestinal tract and other organs of each marine animal, and later existed unrestricted within the homogeneous biomass. Since an overwhelming majority of marine animals are carnivorous, their fermentative system effectively completes the task of self-digestion. The best candidates for completing such a process are fish and particularly, marine organisms of northern waters, or those inhabiting a colder climate. This is because their fermentative system is more robust since it is forced to trigger proteolysis at a lower temperature. Consequently, in the proteolytic fermenter, ferments of animals from colder climates complete proteolysis more effectively than ferments of organisms from warmer climates. The digestive enzymes vary among all animals, including fish. Some of the more potent proteolytic enzymes in fish include, trypsin, chymotrypsin, etastase, collagenase, amino peptidase, and carboxypeptidase. Even among marine animals, the proteolytic enzymes vary. For example, North Atlantic and Antarctic krill have a potent proteolytic, enzyme, euphanciaceae, and Atlantic salmon have serine protases.

Enzymatic protein hydrolysate ("EPH") is the main product of the proteolytic fermentation process of the present invention. This product can change its form if the proteolytic fermenter is used in combination with a device that divides the enzymatic protein hydrolysate into separate components. Together, the two mechanisms compose a device for obtaining free amino acids. Instead of the ferments that arrive with the homogenized biomass, the proteolytic fermenter can use special, previously extracted and immobilized ferments. In this case, the machine can be utilized for the decomposition of distinct, specific types of proteins. The amino acid content produced by the protein hydrolysate will be the characteristic protein-specific or organ-specific array of amino acids. Such a device based on the proteolytic fermenter is called the device for selective protein-specific fermentative biodeconstruction. If a specific organ is used as input material for fermentative biodeconstruction, the mechanism will be called the device for selective organ-specific fermentative biodeconstruction. Moreover, the proteolytic fermenter may be used for the modification of certain substances that contain proteins. For instance, if chitin is used as an input into the proteolytic fermenter with immobilized ferments, ensuring the process of proteolysis, the protein ingredient of chitin will be lost. The product of such a biotechnological reaction is known as chitosan. It has a number of unique properties, including the ability to effectively absorb metals contained in seawater. The mechanism for obtaining chitosan based on the proteolytic fermenter will be called the biomodifier. With the aid of a biomodifier, other substances may be obtained: high-quality cod-liver oil, minerals, or vitamins.

Any existing type of food may be enhanced with free amino acids. A synthetic type of food may also be created when amino acids combine with carbohydrates, lipids, vitamins, minerals, bioactive substances, and fiber. Other combinations are feasible—for instance, amino acids with fiber, amino acids with vitamins and minerals, amino acids with lipids and minerals, etc. The food may have a variety of purposes: balanced food in case of medical treatment where the array of available amino acids is tailored to the patient's needs. Let's take as an example the food for those suffering from hypertonic disease, following a myocardial stroke or for those suffering from diabetes. The use of pure amino acids permits us to shift the energy balance from carbohydrates within the diet to amino acids and lipids, lowering the stress exerted on the insulin apparatus. In most cases of diabetes, it is sufficient to shift the patient's dietary emphasis towards amino acids for a complete correction of the pathological process and pathological status of the patient.

EPH is a nutrient medium and "growth" supplement for the intensive growth of microorganisms that produce methane and other natural gases. The addition of EPH into the reproduction phase, growth phase, and/or decline phase of biological organisms that produce methane from coal, including brown coals, lignites and related carbonaceous materials, in retorts or other vessels after coal is extracted from the ground will enhance the speed and efficiency of the methane production process.

Figure 8:
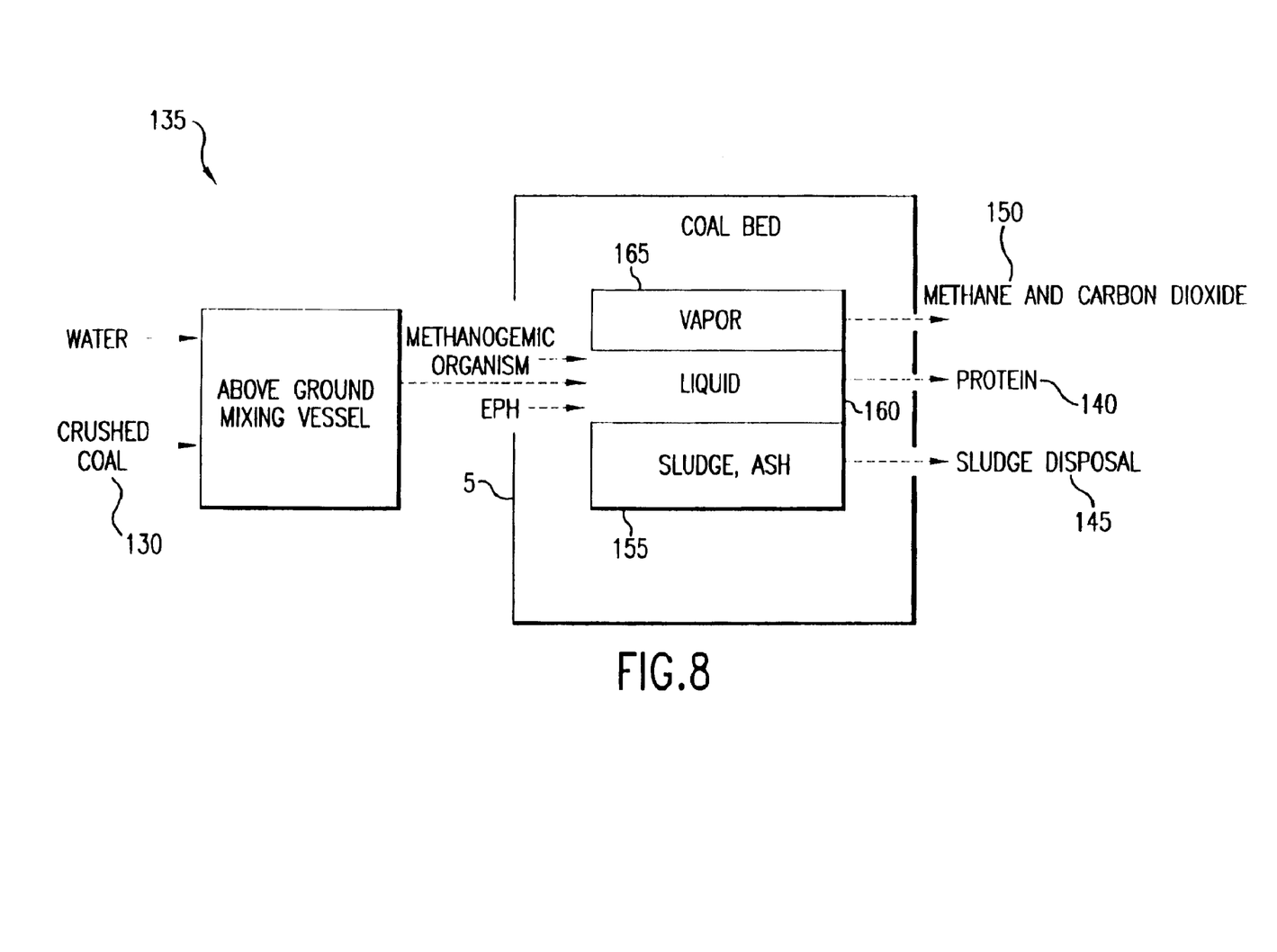
FIG. 8 is a block diagram showing the use of EPH as an accelerant in the production of coal bed methane.

Referring to FIG. 8, injection of EPH and one or more types of methanogenic organisms, will provide free amino acids, along with a variety of minerals and vitamins, that will enable the organisms to reproduce, grow and proliferate without the limitations imposed by a severe lack of naturally occurring free amino acids in the coal. The need to add methanogenic organisms depends on how effective indigenous microflora are in bioassimilating coal. EPH will accelerate the rate of gas production due to the enhanced quantity of organisms and their relative strength. The concentration of EPH added to liquid 160 within coal bed 5 will be less than 4%, and typically below 1%. Methane and carbon dioxide 150 are collected from vapor 165 while sludge, ash 155 can be removed to maintain sufficient void space for the transport of gas to the surface.

The process to use certain anerobic bacteria to gasify lignite has been described in U.S. Pat. No. 6,143,534, by Menger, et al, which is hereby incorporated by reference in its entirety. It is not proven whether combining EPH with the process described in U.S. Pat. No. 4,540,666 will accelerate bacterial growth. It is an object of this invention to disclose an industrial method and apparatus for the digestion of proteins—using naturally occurring enzymes—into free amino acids and short, biologically active peptides.

It is another object of this invention to solve the problem of harvesting, accumulating and utilizing the entirety of fish to produce amino acids and other nutrients, including hydroxylapatite, fish oil, calcium phosphates, and an enzymatic protein hydrolysate.

It is yet an additional object of this invention to solve the problems of drying and separating the components of an enzymatic protein hydrolysate.

It is yet another object of this invention to produce an enzymatic protein hydrolysate employing both farmed fish and computerized control of the hydrolysis process, such that even greater consistency is present in the hydrolysate and in the final product.

It is a further object of this invention to produce an enzymatic protein hydrolysate from cold water fish that can be used as a nutritious medium for cellular and bacterial growth in other industrial processes.

DESCRIPTION OF THE PREFERRED EMBODIMENTS

The basis of the industrial technology of the present invention is the fermentative hydrolysis of protein from a variety of salt-water fish. The hydrolysis is carried out under moderate conditions that imitate the physiological environment within the intestine of mammals and birds during digestion. Like the meat from farm animals and poultry, fish is a valuable food product and a source of biologically active substances. Hence the wastes from the fish processing industry—substandard fish, heads, tails, fins, entrails, skin and blood—may be used as a protein substrate for hydrolysis in the production of high-quality nutrient media. More than 70 million metric tons of fish annually come from the world's oceans. 35–50% of its total amount is lost as waste products (heads, bony skeletons, viscera) are typically considered substandard raw materials. A large share of the waste is thrown overboard into the sea. Some is processed to produce fish meal usable as fodder for feeding animals. However, taking into consideration the composition and nutrient value, fish waste products are in no way inferior to fish meat. The amino acids factory shown in FIG. 1 capitalizes on the concept that fish entrails, particularly cold-water fish entrails, containing hardy enzymes that can actively hydrolyze proteins under cooler temperatures and mild pH, may be used as an efficient ferment in the proteolytic break down of whole fish.

Meat from fish contains 12.4–23.9% raw protein, depending on the species. The proteins from fish are similar to the proteins from the meat of land animals in regard to their fractional and amino acid compositions. The content of water soluble proteins is as high as 30% in individual species of fish; the concentration of salts, which can be extracted with solutions, can reach 75%; the concentration of insoluble salts is from 3% to 10% in bony and cartilaginous fish, respectively. The meat from fish (Cod) contains 2.5% free amino acids. Most of this pool is made up of basic amino acids, glycine, alanine, as well as beta-alanine, and taurine. The flesh from fish with white and dark coloring differs sharply in regard to histidine content. The histidine concentration in the former does not exceed 7%, while the concentration in the latter is from 30% to 80% of the total composition of free amino acids, or 2% of the weight of the meat. Histidine undergoes decarboxylation during storage, with the formation of histamine, which is responsible for the clinical manifestation of allergic reactions and is a cell poison. A specific component of fish meat is the amino acid taurine—a product of the decarboxylation of cysteic acid—and typically not present in the meat of land mammals. The other low molecular weight nitrogenous compounds in fish include: creatine and creatinine, the dipeptides anserine and carnosine, and the tripeptide glutathione. Scientific data attest to the fact that the amino acid compositions of meat from various species of cold water fish (whole fillets) do not differ a great deal, although certain variations, such as a high histidine content in the meat of the mackerel (twice the average level), are observed. There is a difference in enzyme content of the entrails between cold water fish and warm water fish, and a slight differences in enzyme content beteen the various types of cold water fish.

The main nutrients in fish hydrolysate, according to the present invention, are amino acids, which are the structural units of proteins and, accordingly, the building blocks for their construction. The muscle and connective tissues of the body, all the organs of the body, the blood, the brain and the glands for internal secretion are made of proteins; all the extracellular and intracellular enzymes are proteins; most of the hormones are peptides (protein fragments); the transfer of energy, information and oxygen in every living cell is performed by proteins. However, in addition to their plastic function, the amino acids play an additional, independent role in various processes in the body and have independent biological activity of their own. For hydrolysates to be used for most purposes, they must have a balanced amino acid composition and must contain essential amino acids in the quantities necessary for the body. The essential amino acids for most species of higher and lower animals are arginine, valine, histidine, isoleucine, leucine, lysine, methionine, threonine, tryptophan and phenylalanine. The nonessential amino acids are the most active participants in many metabolic reactions and act as links in metabolic pathways.

Figure 1:
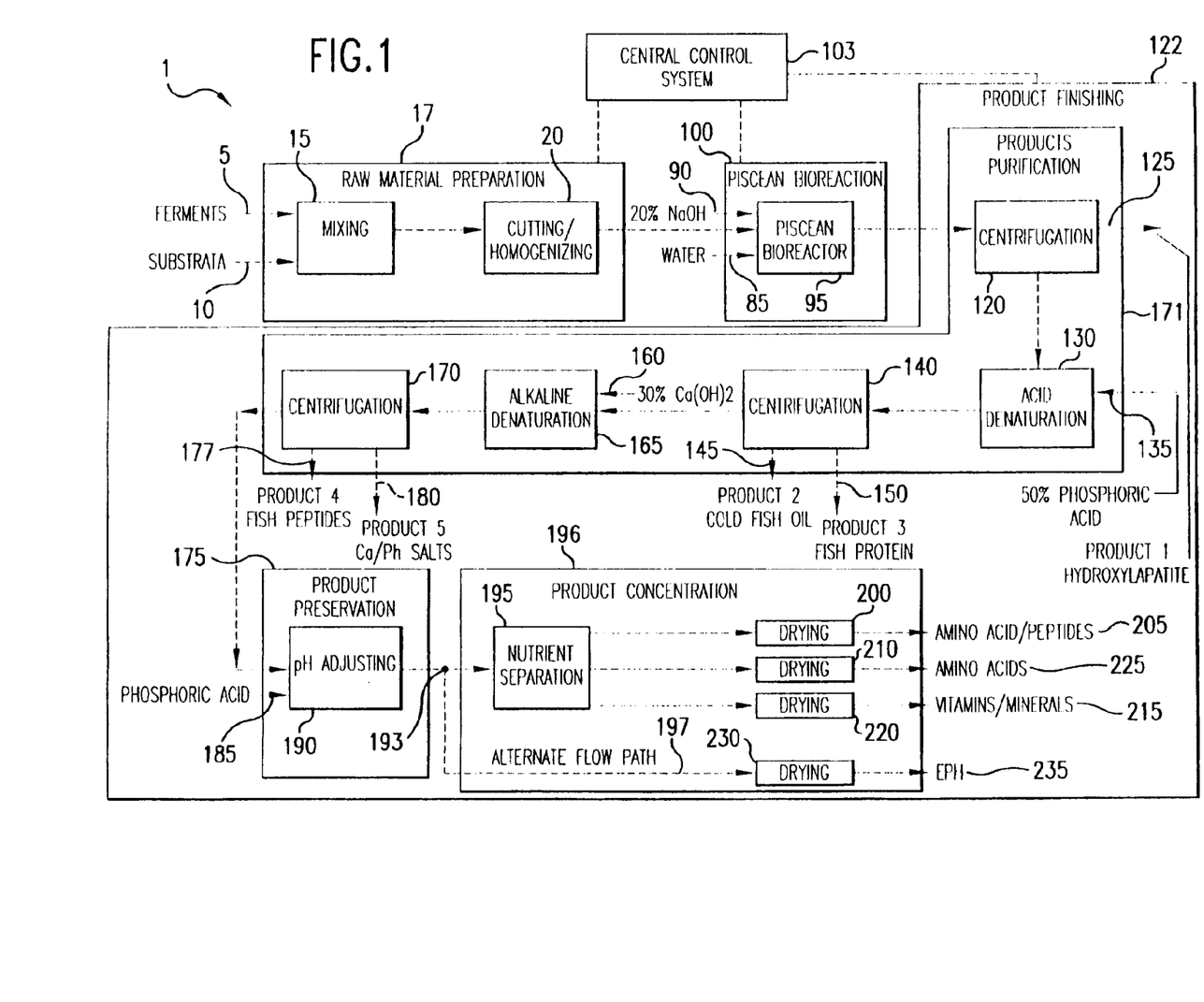
FIG. 1 is a diagrammatic view of the amino acids factory.
Figure 2:
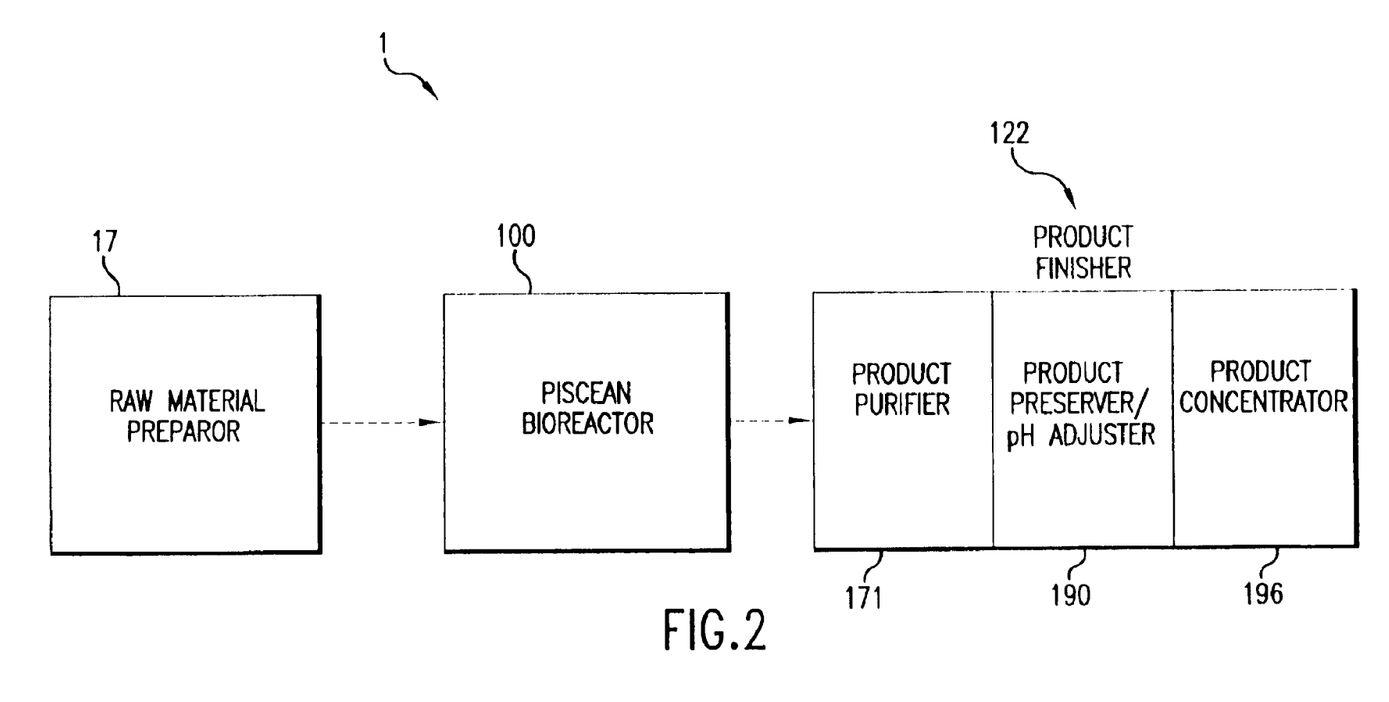
FIG. 2 is a simplified block diagram of the amino acids factory of FIG. 1.

Referring to FIG. 2, the preferred amino acid factory comprises a raw material preparor 17, a piscean bioreactor 100, and a product finisher 122. These three components further contain subcomponents as shown in FIGS. 1–4 and as described below.

Since an overwhelming majority of marine animals are carnivorous, their fermentative system effectively completes the task of self-digestion. The best candidates for completing such a process are fish and other marine organisms of northern waters, or those inhabiting a colder climate. Their fermentative system is forced to trigger proteolysis at a lower temperature. Consequently, ferments of cold water animals complete proteolysis more effectively than ferments of organisms from warmer climates, even at relatively low temperatures.

Referring to FIGS. 1 and 2, raw material preparor 17 includes a mixer 15 and a cutter/homogenizer 20. The raw materials entering mixer 15 include ferments 5 and substrate 10. In the preferred embodiment, substrate 10 is a single type of cold water fish, preferably whole, uncut farmed salmon. However, the substrate may be any cold-water marine animal. Preferably the protein source is "farmed fish"—again, preferably salmon. However, trout, halibut, and tappai may be used. "Wild catch"—such as cod, mackerel or herring may also be used as a substrate. The substrate may also be "pelagic fish," or it may be "industry fish"—preferably such as blue whiting. Shrimp, krill, and blue mussels may also be used as a substrate in the bioreactor. Blue mussels have a high chitin content. The above list of substrates is not exhaustive, however, the listed source materials represent cold water fish protein available in commercially significant quantities.

External objects or materials must never be admitted into the fish by-products. Prior to the loading of raw materials into a grinder, it is necessary to prepare a mixture of tissues containing ferments (internal organs of fish) as well as tissues that provide protein for hydrolysis ("technical" fish: whole fish, heads, tails, skeleton parts, etc.). For complete and profound hydrolysis, an optimal ratio of substrata to ferments has been experimentally selected. It is the ratio of the weight of substrata containing fish tissues to the weight of ferment-containing tissues. For freshly frozen raw materials, this ratio is 1:1. The resulting homogeneous mass (of ferments and substrate) is transported into the bioreactor, where it is combined with water at a 1:1 ratio in terms of weight. In this manner, 5 tons of raw materials (2.5 tons of fish internal organs and 2.5 tons of other fish tissues) and 5 tons of water are loaded into a reactor with a 10-ton capacity. That is, in the preferred bioreaction, the total mass of ferments 5 is equal to the total mass of substrate 10.

Ferments 5 preferably come from a specific fish type, and preferably from a specific region or catch. Farmed fish, such as salmon, are optimal for both substrate and for ferment because farmed fish enable greater enzyme consistency in bioreactor 100. In one embodiment, the ferments consist of a specific organ. The resulting EPH mix would include an organ-specific array of amino acids. In another embodiment, the ferments may be synthetic derivatives of cold water fish enzymes, unique or cloned, of any origin. In yet a further embodiment, special, previously extracted and immobilized ferments may be used in place of raw entrails. Pure, deboned fish meat (fillets) may alternatively be used as the substrate. Where pure fish meat and immobilized ferments are utilized, several steps of the factory may be eliminated.

Figure 5:
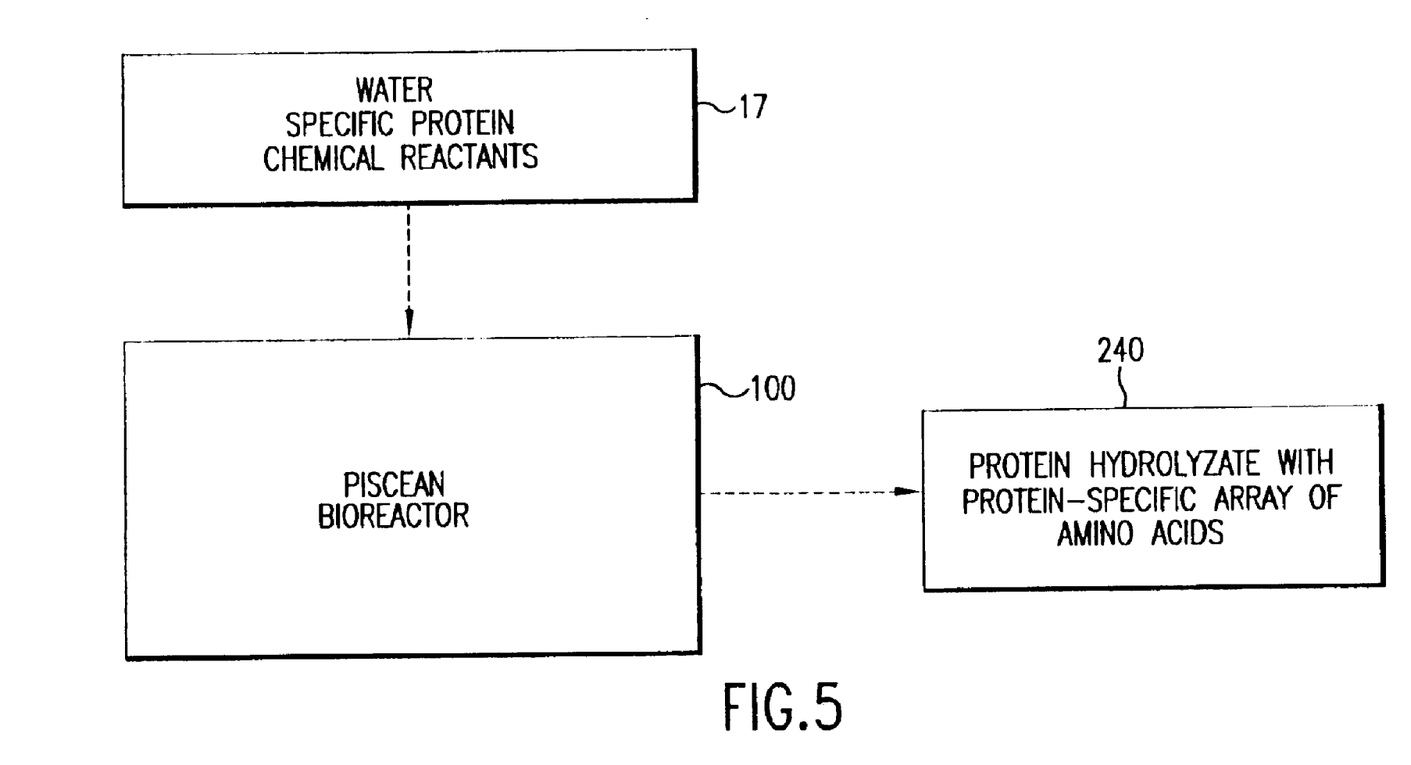
FIG. 5 shows an amino acid factory using a protein-specific array of amino acids.
Figure 6:
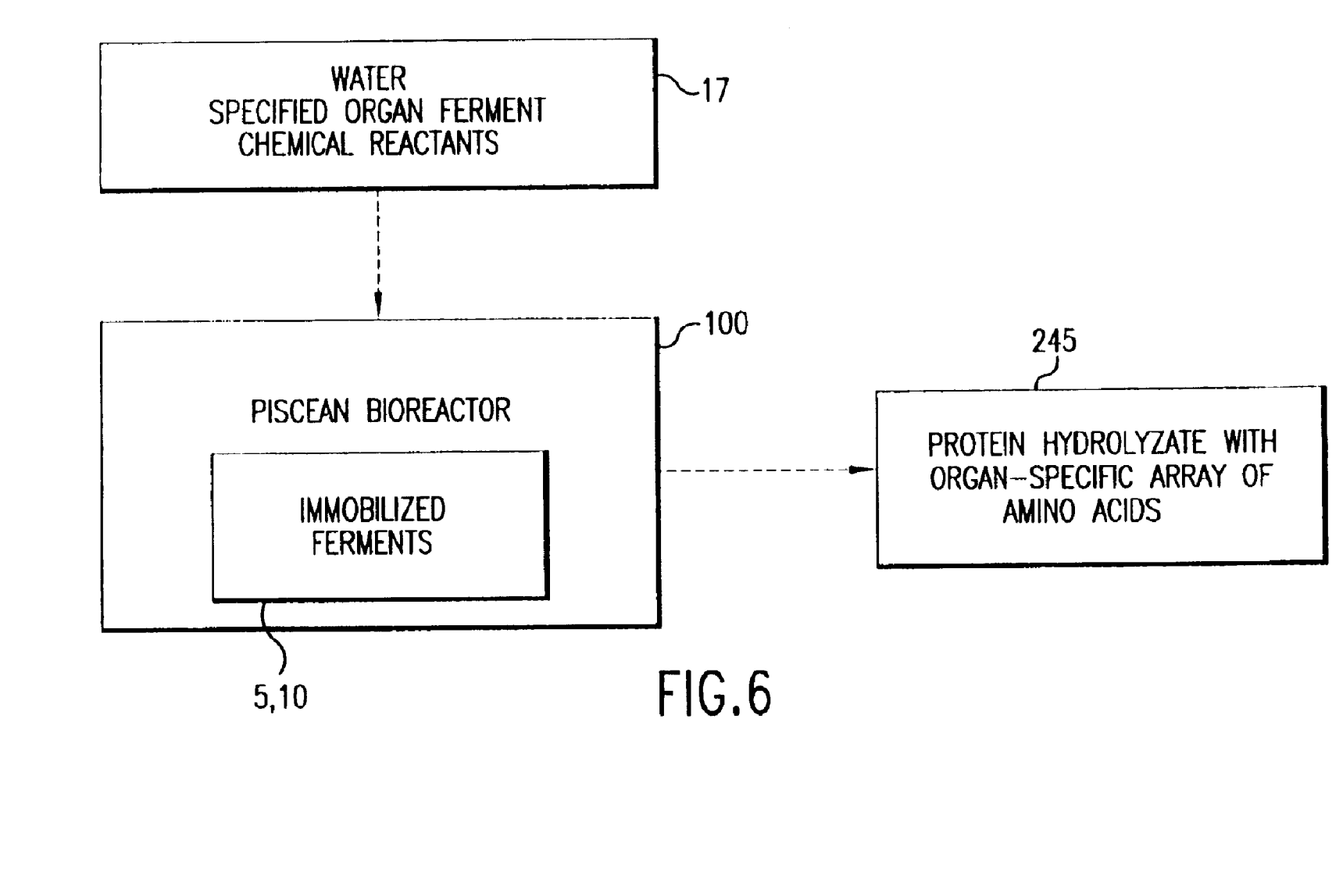
FIG. 6 shows an amino acids factory producing an organ-specific array of amino acids.
Figure 7:
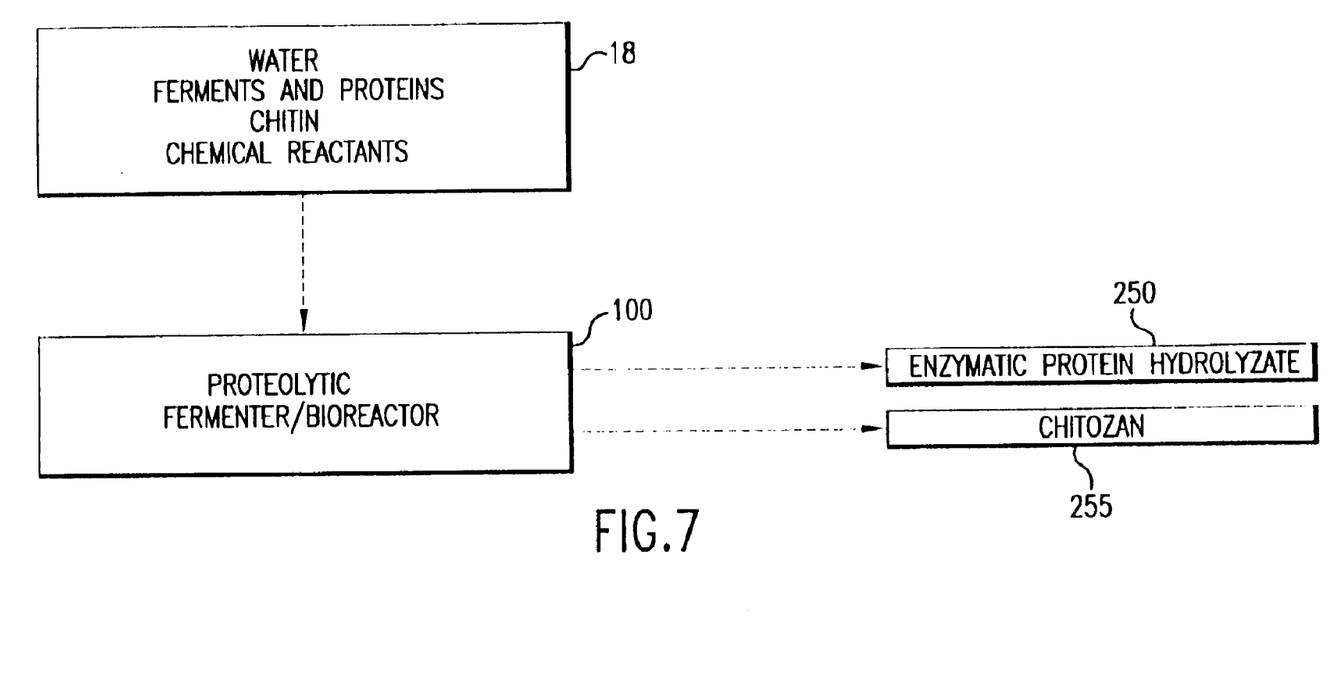
FIG. 7 shows an amino acid factory that produces enzymatic protein hydrolysates in addition to Chitozan.

In another embodiment as shown in FIG. 5, amino acid factory 1 may be utilized for the decomposition of distinct, specific types of protein ferments. As shown in FIG. 5, the amino acid content produced by the protein hydrolysate would reflect the protein-specific array of amino acids from a particular source. Such a device based on the proteolytic fermenter will be called the device for selective protein-specific fermentative bioconstruction.

Referring to FIGS. 1 and 2, before input into bioreactor 100, raw materials 5 and 10 must be broken up with an industrial mixer 15 and reduced to an homogeneous mass. Size reduction equipment in cutter/homogenizer 20 must be designed to produce a homogenous mass of fish remnants such that a typical particle size of 0.1 mm to 0.3 mm results. Preferably, cutter/homogenizer 20 is of stainless steel construction but may be of any other suitable construction known in the art. Blade 25 can be rotary knife type or granulator type as long as size requirements are met.

After the material is homogenized, fermentative deconstruction of the proteins begins in bioreactor 100, sometimes referred to herein as a proteolitic fermenter, or reactor. Preferably, bioreactor 100 is a glass-lined, jacketed reactor with integral impeller (20–25 rpm). The main body is preferably carbon steel, but may be constructed of any other material suitable for containing upwards of ten tons of liquid material. Connection nozzles are required for addition of fish remnants, water, and pH adjustment chemicals. Connection nozzles are also required for passing steam or cooling water through the reactor jacket. Bioreactor 100 may be of any shape, including rectangular, or tubular, and is restricted by walls of any appropriate smooth surface material—glass, stainless steel, plastics, preferably inert composites—that may be easily cleaned and that are not readily subject to oxidation or enzymatic migration of elasticizers. Preferably bioreactor 100 has a capacity of at least five tons, but may have up to a twenty ton capacity. Specifics of its construction allow for this capacity to contain the necessary material for the large-scale biodeconstruction of proteins.

Input materials for bioreactor 100, in addition to including homogenized substrate and ferments, consist of water 85, and chemical reactants 95. Preferably water 85 is deionized and distilled to minimize contaminants. In the preferred embodiment, the mass of water is equivalent to the combined mass of ferments and substrate. The operating temperature may ranges from 20 to 100 deg. C., but preferably the hydrolysis takes place at between 44.5 and 45 degrees C. Through bioreactor 100, the raw materials begin transforming into a protein hydrolysate. The required alkalinous environment in the bioreactor is created using fractional automatic addition of 20% NaOH solution to the mixture being hydrolyzed. The quantity of NaOH solution may vary greatly and depends on the level of acidity and the buffering capacity used in the technological process of tap water. Hydrolysis takes place for a maximum of three hours due to the risk of bacterial growth, accompanied by excessive production of foam. Hydrolysis is carried out given a continuous automatic correlation between the pH and temperature levels. Laboratory control of the hydrolysis, every 30 minutes, is accomplished by monitoring the accumulation of amino-azote in the hydrolysate using formol titration. The completion of hydrolysis is confirmed when the level of amino-azote remains the same between lab tests or grows by a maximum of 5–7%. Hydrolysis is discontinued by the thermal coagulation of contents in the hydrolysate (+95° C., 10 min.). This is accomplished by directing steam through the outer cover of bioreactor 100 and simultaneous intensive blending of its contents (20–25 rpm.) Then, the contents of bioreactor 100 are cooled to +60° C. by allowing cold water to flow between its outer cover and reactor itself.

Upon completion, contents of the reactor are made up of the following components: oil, together with a fraction of light lipo-proteins, bone tissue (hydroxilappatit), and a water-based mixture of hydrolyzed proteins. Since 18% of fish tissue is protein, in excess of one ton of protein is hydrolyzed from a mass of raw materials that weighs 10 tons. Hydroxilappatit 125 represents significant economic value as a mineral food supplement for people, or in animal feed. For this reason, bone tissue is transported into a separate tank, repeatedly subjected to a decanter in water, separated, dried, minced, and packed. Centrifuge 120 is a high speed decanter for separating bone tissue from hydrolysate. Centrifuge 120 is preferably made from stainless steel and has a nominal rotation speed of 6,000 revolutions per minute. The product of centrifuge 120 is hydroxylapatit 125, which is 25% of the raw materials being hydrolyzed.

After the bone tissue has been separated, the hydrolysate may also be cleaned of cod-liver oil. However, in this case, the oil will be highly contaminated by fragments of low-density lipo-proteins, which are difficult to eliminate during the cleaning of cod-liver oil. These fragments are denaturated in an acidic environment and then separated from cod-liver oil. Acid denaturation enables separation of highly molecular peptides, glycoproteides, lipoproteides, and nucleoproteides. First denaturating tank 130 (acid denaturation vessel) is preferably a glass-lined, jacketed vessel with an integral impeller. The main body of tank 130 is preferably carbon steel, but may be any other suitable material. Tank 130 has a connection nozzle for the addition of a phosphoric acid solution. There are also connection nozzles for passing steam or cooling water through the jacket of tank 130. There is a discharge nozzle for the denaturated hydrolysate at the down stream end of tank 130. Although other solutions may be used, the combination of NaOH in bioreactor 100 and phosphoric acid in tank 130 is optimal for this enzymatic hydrolysis. Acidic denaturation is a necessary procedure in the process of cleaning the hydrolysate and serves the purpose of freeing it from unhydrolyzed cellular remains and highly molecular products of hydrolysis. The pH level of the bioreactor's contents is brought to 3.5 by fractional automatic addition of a 50% phosphoric acid solution and later heating to +90° C. This temperature is maintained for 15 minutes and then the contents are cooled down to +60° C. The entire procedure of acid denaturation is accompanied by continuous mixing of the bioreactor's contents at 10–12 rpm. The mass of denaturalized fish proteins (highly molecular peptides, glycoproteides, lipoproteides, and nucleoproteides) is separated from the hydrolysate using a high-speed decanter. After that, the hydrolysate is replaced into the bioreactor.

Still referring to FIG. 1, second centrifuge 140 is a high speed liquid solid separator for separating cold fish oil 145 and fish protein 150 from the hydrolysate. Preferably it has a disc or cell operating at 7,000 revolutions per minute. Fish protein represents significant economic value as a source of food as well as a food supplement. For this reason, the fish protein is transported into a separate tank, repeatedly subjected to decanting in water, separated, dried, minced, and packed. It is possible to pack the protein in batches and to distribute it to the consumer in either fresh or frozen state. The resulting protein weighs 0.3–0.4 tons (net weight) out of the 5 tons of raw materials that undergo hydrolysis. Oil is disconnected from the hydrolysate by way of high-speed separation, at a temperature of 60° C. is pumped through a standard separator such as that which is used in the dairy processing industry. A high speed separator operating at 7,000 rpm is used. Fish oil also represents significant economic value as an independent product. For this reason, the oil is transported into a separate tank and, as it collects, the oil is subjected to additional cleaning, rectification, amalgamation, and packaging. The resulting cold fish oil 145 weighs approximately 1 ton out of the 5 tons of raw materials that undergo hydrolysis.

Second denaturating tank 165 is an alkaline denaturation vessel with an operating pH optimally of 8.5. It is preferably a jacketed reactor with integral impeller operating optimally at approximately 10–12 revolutions per minute. The main body may be steel or other suitable material, and it has an operating temperature range from 20 to 100 degrees C. Tank 165 should have connection nozzles for the addition of hydrolysate and preferably a calcium hydroxide Ca(OH)2 solution having a concentration of approximately 30 percent. It also has connection nozzles for passing steam or cooling water through the jacket. Separation of Calcium-dependent highly molecular peptides is accomplished througth alkalinous denaturation in the presence of Ca ions. This ensures a more complete cleansing of the hydrolysate from highly molecular peptides (80,000 D–30,000 D), as well as from a significant portion of the normally molecular peptides (30,000 D–5,000 D). Hydrolysate in the bioreactor is neutralized and then alkalized to a pH of 8.5 using fractional automatic addition of preferably a 30% water-based Ca(OH)2 mixture, heated to +90° C., maintained at that temperature for 15 minutes, and then cooled to +60° C.

The advantage of using both alkaline and acid denaturation is that their combination helps to maximize the removal of unwanted by-products of the hydrolysis reaction. These steps also help to improve the efficiency of additional separations processes designed to concentrate the various constituents into distinct product streams.

Referring again to FIGS. 1 and 2, the final component of product purifier 171 is third centrifuge 170, a high-speed decanter for separating denatured fish peptides and phosphorus salts of calcium. Centrifuge 170 has a preferred rotation speed of 7,000 revolutions per minute. Phosphorous salts of calcium represent high economic value as an independent product utilized in the chemical industry. For this reason, they are centrifuged and harvested. As the contents accumulate, they are dried, freed from organic matter (by way of incineration), batched, and packed. The resulting phosphorous calcium salts (together with calcium hydroxide) weigh approximately ⅓ ton when the hydrolisate is cleaned from 5 tons of raw materials.

Referring still to FIG. 1, pH adjuster 190 is a carbon steel mixing tank with integral impeller and an operating pH of 5.5. It operates preferably at ambient temperature, and has a connection nozzle for the addition of a mild phosphoric acid solution. The main function of pH adjuster 190 is to aid in product preservation.

As shown in FIG. 2, the final component of product finisher 122 is product concentrator 196. Usually the hydrolysate is concentrated 3–4 times, because as the concentration of a solution increases, their solvency and hydrophobic bonds decrease. At the end of the concentration process, a pH level of 3.5–4.0 is established, which inhibits the growth of microflora. Concentrator 196 includes nutrient separator 195 and alternate driers 200, 210, 220, and 230. Separator 195 is in communication with pH adjuster 190 through flow redirector 193. Flow director 193 permits production of either an EPH liquid 197, an EPH powder 235, and/or at least three other products. These include an amino acid/peptide mix 205, a vitamin/mineral mix 215, or pure amino acids 225. Nutrient separator 195 can be one of a number of unit operations that can separate one or more amino acids, peptides, and vitamins and minerals from the EPH solution produced by the piscean bioreaction. Nutrient separator 195 may entail ultra-filtration, piezo-dialysis, or countercurrent extraction of nutrients, as appropriate, in order to produce mixtures that consist mostly of one or two constituents of EPH.

In a piezo-dialysis unit, as described in U.S. Pat. No. 4,554,376, by Fujimoto, which is hereby incorporated by reference in its entirety, an amphoteric ion exchange membrane is used to separate a specific amino acid. Dialysis is carried out at the isoelectric point so that a low molecular weight electrolyte, which is contained as an impurity in the amino acid solution or an amino acid which is not at its isoelectric point, can be selectively allowed to permeate while an amino acid which is at its isoelectric point will not.

In ultra-filtration, a synthetic membrane that allows only certain size spherical molecules to permeate (typically 2,000 Daltons to 1,000,000 Daltons) is used to remove relatively high molecular weight solutes and particulate components from water and other solvents.

In countercurrent extraction, an organic phosphorous acid extractant, as described in U.S. Pat. No. 5,049,279, by Bitar, et al, which is hereby incorporated by reference in its entirety, is used to collect certain amino acids into an extractable liquid phase where transfer into an aqueous phase is possible. The aqueous phase is then charged with hydrochloric acid, producing an acidic concentrated solution of the target amino acid.

Figure 4:
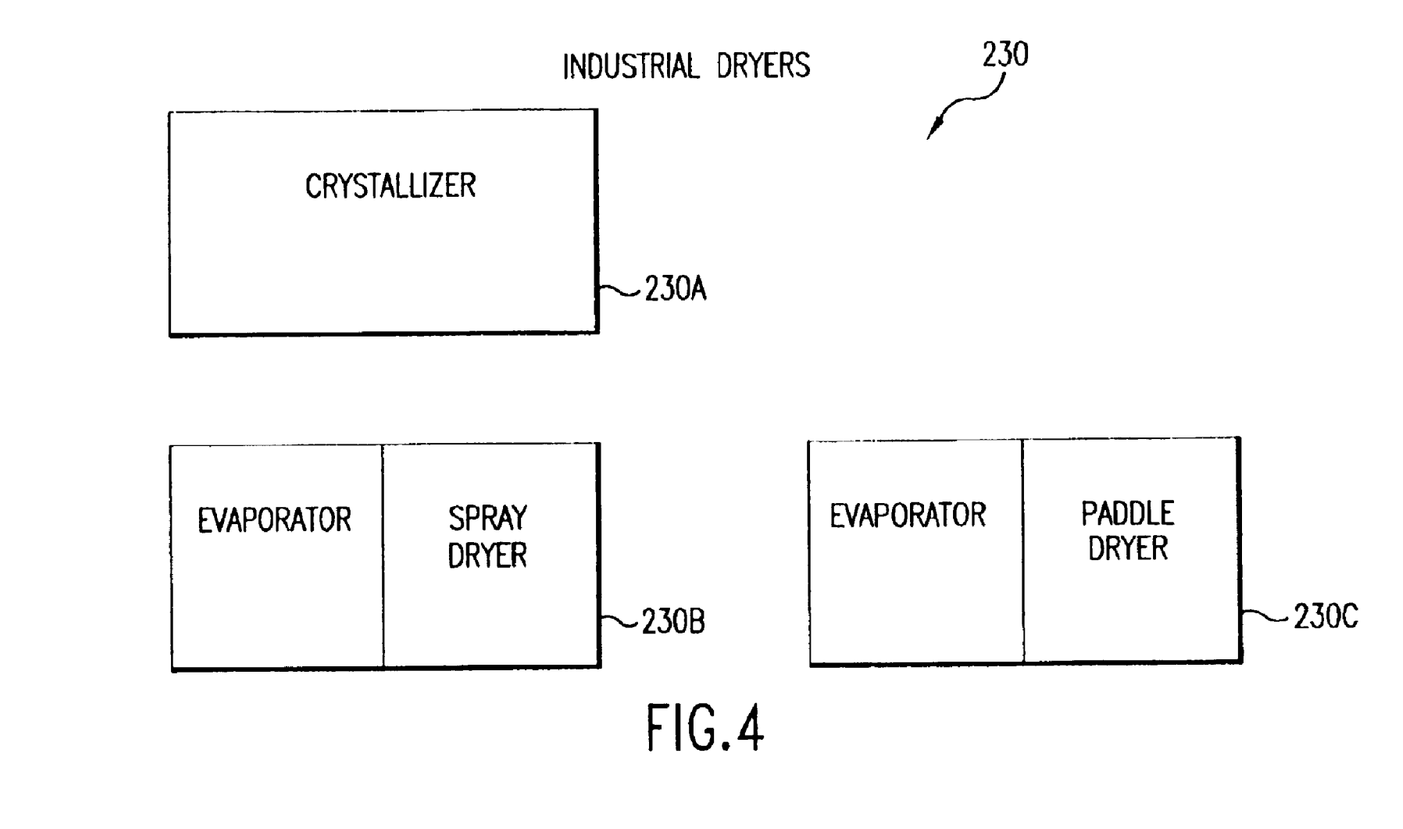
FIG. 4 shows alternate dryers for use in the amino acids factory.

Dryer technology is critical to the success of amino acids factory 1. The preferred embodiment is an evaporator followed by an industrial paddle-type dryer 230. Referring to FIG. 4, an evaporator/paddle dryer is a two step process. Evaporator 230B may be either a once-through unit (agitated film, falling film, or climbing film), or a circulation unit (short-tube, forced-circulation, or climbing film). In once through operation, the feed liquor, or hydrolysate passes through a series of tubes with condensing steam providing the heat required for evaporation. The feed hydrolysate leaves the unit as a thick liquor. The evaporation is accomplished in a single pass. In circulation evaporators a pool of liquid is held within the equipment. Incoming feed mixes with the liquid from the pool, and the mixture passes through the tubes. Unevaporated liquid discharged from the tubes returns to the pool, so that only part of the total evaporation occurs in one pass. The general purpose of the evaporator is to concentrate the EPH solution prior to final drying.

In a paddle dryer 230C liquid EPH is forced into one end of a chamber. Hot air is injected downward into the liquid material through a horizontal screen, which causes bubbling of the EPH liquid and granulation. Below the screen is a paddle chamber where multiple-paddles mounted on rotating axels continuously scoop up dried granules and move them towards a discharge chute, where the granules are conveyed. An enclosed chamber above the air nozzles provides freeboard for entrained dry particles to settle back into the mixing area.

There are several advantages of this type of dryer, patent pending in Norway by Drytec. Paddle dryers operate in a temperature range from 150° C. to 200° C. using hot air rather than steam. The paddles provide better mixing and fewer hot spots, resulting in less damage to the EPH powder, and a higher quality product than is the case with conventional drying technology.

Referring to FIG. 4, alternate dryers that may be used with factory 1 include a crystallizer 230A, and an evaporator/spray dryer 230B to produce EPH in dry powder form. Crystallizer 230A is equipped with a draft tube, which also acts as a baffle to control the circulation of the magma, and a downward-directed propeller agitator to provide a controllable circulation within the crystallizer. An additional circulation system, outside the crystallizer body and driven by a circulating pump, contains the heater and feed inlet. Product slurry is removed through an outlet near the bottom of the conical lower section of the crystallizer body. For a given feed rate, both the internal and external circulations are independently variable and provide control for obtaining the required crystal size distribution.

Regarding spray dryer 230, the concentrated EPH from the evaporator 230B is dispersed into a stream of hot gas in the form of a mist of fine droplets. Water is rapidly vaporized, leaving residual particles of dry EPH, which are then separated from the gas stream. The flow of EPH and gas (steam or hot air) may be cocurrent, countercurrent, or a combination of both in the same unit. The droplets are formed inside a cylindrical drying chamber, either by spray nozzles or by high-speed spray discs. The drying chamber is typically large (8 to 30 feet in diameter) to prevent the droplets from touching a solid surface before drying has taken place.

As shown in FIG. 1, enzymatic protein hydrolysate ("EPH") is the main product of amino acids factory 1. As previously detailed, other products are derived upstream from nutrient separator 195, including hydroxylapatit 125, cold fish oil 145, fish protein 150, phosphorous salts of calcium, and fish peptides 177. Although part of the novelty of the amino acid factory is the number of different products derived from essentially a singular input source (fish and water), the key product and most commercially valuable nutrient produced by amino acid factory 1 are amino acids and the enzymatic protein hydrolysate (EPH) powder 235, finished through drier 230. EPH consists of 70 to 90 percent free amino acids, 15 to 25 percent highly molecular peptides, and less than 5 percent vitamins and minerals. A less expensive (liquid) form of EPH may be harvested at 197.

Figure 3:
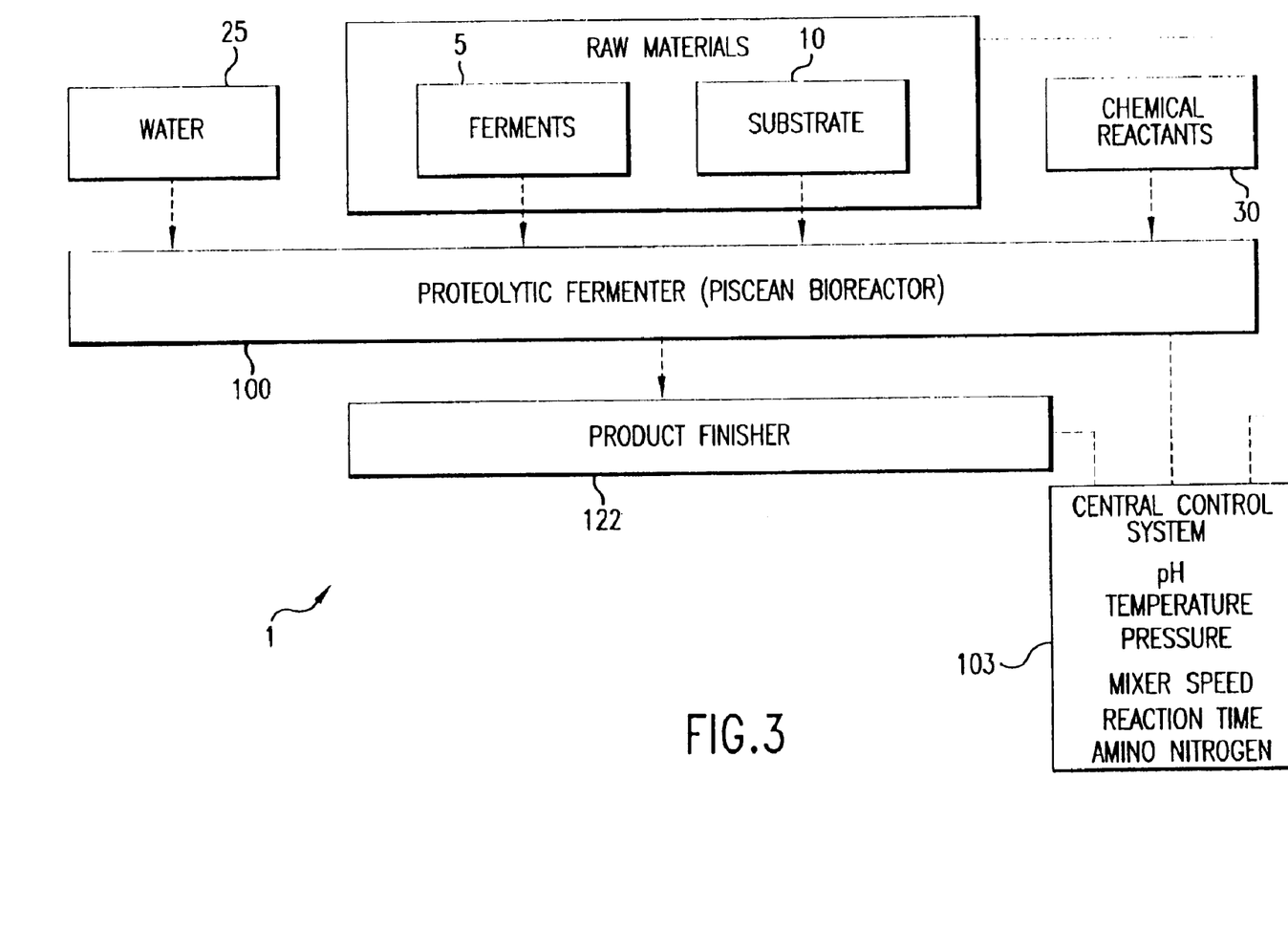
FIG. 3 is a block diagram of the amino acids factory showing automated controls of the hydrolysis.

Referring now to FIG. 3, central control system 103 for the amino acids factory makes use of commercially available instrumentation and control equipment with direct electronic links to one or more computers. This system includes one main and several video display screens to indicate system status and key operating parameters, keyboards and switch controls to adjust operating conditions, a central processing unit (CPU) to process system-derived data in real time, and control interlocks for safety and system shutdown in the event of power failure or other emergencies. The CPU will evaluate all monitored process data, such as pH, temperatures, pressures, etc. and convert them to the appropriate mechanical or chemical task required to maintain the process within specified operating ranges through the use of appropriate software. In general, this system will perform the following: a. monitor and display the status of each key piece of equipment in the production process during the manufacturing sequence; b. maintain key operating parameters within their proscribed limits; c. provide alarms during process upset conditions; d. increase the level of process automation during process startups; and e. increase the level of process automation during process shutdown.

According to the preferred embodiment, operating data is fed to process control system 103 from monitoring instruments located throughout the factory. The manufacturing process consists of three principal procedures. These are: a. raw material preparation, b. piscean bioreaction, and c. product finishing. Each of these three principal procedures consists of one or more distinct unit operations that are required to convert one of a number of fish types (e.g., salmon, trout, halibut, tappai, cod, mackerel, herring, shrimp, krill, and blue whiting) into commercial products.

A description of the inputs processed by control system 103, the subsequent outputs, and their relation to providing overall process automation, safety, and ease of operation, is as follows: For raw material preparation, the data inputs for this procedure include: fish type (only one type of fish may be used per batch); the total weight of fish remnants charged to the cutter/homogenizer; and the operational status of the weigher/mixer and cutter/homogenizer. Ferments and substrata from a single fish type are fed to a mixing vessel mounted on an industrial scale to ensure that the 1:1 weight ratio of substrate to ferments requirement is met, and to determine the total weight of the batch to be processed. The resulting mixture then undergoes size reduction in a cutter/homogenizer to produce a homogeneous mass of fish remnants. The outputs from control system 103 will be: display of ON/OFF status for the weighing/mixer and the cutter/homogenizer, the type of fish being processed and the total weight of the batch (displayed on main and local control panels).

The data inputs for the (second) principal procedure include: the type of fish being processed, the weight of the batch to be processed, the pH of the bioreaction mixture, the temperature of the bioreaction vessel contents, the bioreaction time, the concentration of amino nitrogen as hydrolysis takes place, and the bioreaction vessel pressure. The weight of the batch of fish remnants (substrata and ferments in a 1:1 weight ratio, respectively) determines the amount of water to be charged to the bioreaction vessel for hydrolysis. The ratio of fish remnants to water is 1:1. The pH of the bioreaction mixture is maintained between 7.8 and 8.0 by the addition of a caustic solution fed by a metering pump controlled by a signal from a pH probe located within the bioreactor. The amount of caustic solution used is dependent on the pH of the local water supply and its buffering capacity. Once the bioreactor is fully charged and the pH is within the desired range, hydrolysis begins. The bioreaction mixture is continuously agitated by an integral mixer. The progress of the bioreaction is monitored by measuring the concentration of amino nitrogen in the bioreactor at regular time intervals. Once the concentration of amino nitrogen begins to level off, hydrolysis is discontinued by raising the temperature of the bioreaction mixture to 95 C over a time interval of approximately ten minutes. This deactivates the enzymes catalyzing the bioreaction and causes thermal coagulation of the bioreactor contents. The bioreactor contents are then cooled to 60 C. In the unlikely event that a batch becomes contaminated, there will be unwanted bacterial growth accompanied by the excessive production of foam. For this reason, the pressure within the bioreactor is monitored to provide pressure relief and system shutdown to prevent it from exploding.

The data outputs from the computerized control system will be: the quantity of caustic solution metered into the bioreactor, agitator speed, the quantity of water to be charged to the bioreactor, the quantity of non-contact steam required to raise the temperature of the bioreactor to 95 C, the quantity of non-contact cooling water required to lower the temperature of the bioreactor to 60 C, signals for the activation of pressure relief valves, safety alarms, and system shutdown should the bioreactor be contaminated and/or generate excessive pressure.

The inputs for the last principal procedure include: the operational status of the hydroxilapatite/EPH centrifuge, the pH of the acid/neutral denaturation vessel contents, the temperature of the acid/neutral denaturation vessel contents, the operational status of the fish oil/fish protein/EPH centrifuge, the pH of the alkaline denaturation vessel contents, the temperature of the alkaline denaturation vessel contents, the operational status of the fish peptides/Ca—P/EPH centrifuge, the pH of the adjusting vessel contents, the temperature of the pH adjusting vessel contents, the temperature of the nutrient separation unit, the pressure (or pressure drop) of the nutrient separation unit, the pH of the nutrient separation unit, the temperature of the dryer, and the pressure drop across the dryer.

Upon completion of hydrolysis, the contents of the bioreactor are fed to a centrifuge for separation and removal of bone tissue (hydroxilapatite). The EPH solution is then fed to the acid/neutral denaturation vessel. Acid denaturation removes a significant portion of high molecular weight peptides, glycoproteids, lipoproteins, and nucleoproteids from the EPH solution. The pH of the denaturation vessel contents is adjusted to 3.5 by the addition of a phosphoric acid solution fed by a metering pump controlled by a signal from a pH probe located within the denaturation vessel. The amount of acid solution used is dependent on the pH of the hydrolysate and its buffering capacity. The denaturation vessel contents are continuously agitated by an integral mixer. Once a pH of 3.5 is maintained, the temperature of the denaturation vessel contents are raised to 90 C and held there for 15 minutes. Then the denaturation vessel contents are cooled to 60 C. Upon completion of acid denaturation, the vessel contents are fed to a centrifuge for separation of cold fish oil, fish protein, and EPH. The EPH solution is then fed to the alkaline denaturation vessel. Alkaline denaturation in the presence of calcium ions provides additional cleansing of the EPH from high molecular weight peptides (30,000 D to 80,000 D), with significant removal of moderate molecular weight peptides (5,000 D to 30,000 D). The pH of the denaturation vessel contents is adjusted to 8.5 by the addition of a 30 percent calcium hydroxide solution fed by a metering pump controlled by a signal from a pH probe located within the denaturation vessel. The amount of calcium hydroxide solution used is dependent on the pH of the EPH and its buffering capacity. The denaturation vessel' contents are continuously agitated by an integral mixer. Once a pH of 8.5 is maintained, the temperature of the denaturation vessel contents are raised to 90 C and held there for 15 minutes. Then the denaturation vessel contents are cooled to 60 C.

Upon completion of alkaline denaturation, the vessel contents are fed to a centrifuge for separation of fish peptides, phosphorus salts of calcium, and hydrolysate. The EPH solution is then fed to pH adjuster 190. Adjuster 190 brings the pH of the hydrolysate to 5.5 using a phosphoric acid solution fed by a metering pump controlled by a signal from a pH probe located within the pH adjusting vessel. The pH adjuster's contents are continuously agitated by an integral mixer. Upon completion of pH adjustment, the EPH is fed to a dryer for the production of dry, powdered product. The drying unit can be any one of a number of configurations that use steam to evaporate the water content of the EPH and produce a dry powder.

An alternate process unit can also be used to provide further separation of EPH into product streams comprised of major EPH constituents. For example, certain specific amino acids may be isolated by the use of an ion exchange resin. Other constituents of EPH, such as bioactive peptides, may be separated by the use of ultra-filtration. Key monitored operating parameters are typically temperature, pressure (or pressure drop), and pH.

The data outputs from the computerized control system will be: display of ON/OFF status for the hydroxilapatite/EPH centrifuge, the quantity of phosphoric acid solution metered into the acid/neutral denaturation vessel, the acid/neutral denaturation vessel agitator speed, the quantity of non-contact steam required to raise the temperature of the acid/neutral denaturation vessel to 90 C, the quantity of non-contact cooling water required to lower the temperature of the acid/neutral denaturation vessel to 60 C, display of ON/OFF status for the cold fish oil/fish protein/EPH centrifuge, the quantity of 30 percent calcium hydroxide solution metered into the alkaline denaturation vessel, the alkaline denaturation vessel agitator speed, the quantity of non-contact steam required to raise the temperature of the alkaline denaturation vessel to 90 C, the quantity of non-contact cooling water required to lower the temperature of the alkaline denaturation vessel to 60 C, the ON/OFF status for the fish peptide/Ca—P salts/EPH centrifuge, the quantity of phosphoric acid solution metered into the pH adjusting vessel, the pH adjuster agitator speed, the quantity of steam required by the dryer to make EPH powder.

The enzymatic protein hydrolysate (EPH), envisioned by the current invention, is produced by profound enzymatic protein hydrolysis of cold water animals. Approximately 70%–90% of that EPH is free amino acids, as itemized below. An alternate mixture of EPH may also contain Tryptophan, OH-proline, OH-lysine. The EPH also contains approximately 10%–20% highly molecular peptides. In addition, the EPH contains approximately 3%–5% vitamins, minerals and oils. The EPH minerals include cadmium, lead, mercury, arsenic, natrium, potassium, calcium, phosphorous, magnesium, iron, zinc, copper, manganese, selenium, cobalt, molybdenum, chromium. The vitamins in the EPH include thiamine, riboflavin, pantothenic acid, pyridoxine, nicotinic acid, biotin, folic acid, cyanocobalamine, meso-inosite, vitamin E. For each amino acid below, their effect on the functioning of various organs, tissues and systems of the human body, as well as the possible uses of the amino acids in the treatment of specific diseases are briefly described, as follows:

Lysine—$C_6H_{14}N_2O_2$—is an essential amino acid. Promotes the adequate absorption of calcium by bone tissue; participates actively in the synthesis of collagen, which makes up the basis for cartilage and connective and bone tissue; effectively stimulates the synthesis of humoral antibodies and a number of hormones and enzymes. Research has demonstrated that lysine can be effective against the herpes virus, since it stimulates the production of substances that suppress the growth of the virus. A deficiency of lysine in the diet is accompanied by rapid fatigue, an inability to concentrate, irritability, bloodshot eyes, retardation of growth, hair loss, anemia and reproductive problems.

Methionine—$C_5H_{11}NO_2S$—is an essential amino acid. Is the main source of sulfur in the cells of the body, necessary for the normal growth of hair, nails and skin; promotes a lowering of the level of cholesterol in the blood; increases the production of lecithin in the liver; reduces the level of fat in the liver and protects the kidneys; a natural gelatinizing (binding) agent for heavy metals; regulates the formation of ammonia in the urine and promotes the formation of urine without ammonia, which reduces bladder irritation; strengthens the structure of the hair and promotes its growth.

Phenylalinine—$C_9H_{11}NO_2$—an essential amino acid that is used intensively in the brain for the synthesis of norepinephrine—a chemical agent which serves for the transmission of signals between both nerve cells and brain cells; promotes physical activity, reduces hunger, acts as an antidepressant and improves memory.

Threonine—$C_4H_9NO_3$—an essential amino acid. Is an extremely important structural element of collagen, elastin and the proteins that make up tooth enamel; prevents the fatty degeneration of the liver; promotes the normal functioning of the gastrointestinal tract.

Leucine—$C_6H_{13}NO_2$—essential fatty acid that is a decisive component in the synthesis of extremely important biologically active compounds responsible for the generation and transfer of energy in all the cells of the body; stimulates the working of the brain.

Isoleucine—$C_6H_{13}NO_2$—essential fatty acid that is decisive in the synthesis of extremely important biologically active compounds responsible for the generation and transfer of energy in all the cells of the body; stimulates the working of the brain.

Arginine—$C_6H_{14}N_4O_2$—a nonessential amino acid which strengthens the immune response to viral, bacterial and parasitic infections; promotes the healing of wounds and the regeneration of tissues of the parenchymatous organs; inhibits the growth of tumor cells; stimulates the synthesis of growth hormone.

Tyrosine—$C_9H_{11}NO_3$—a nonessential amino acid. Transmits impulses from nerve cells to brain cells; helps to overcome depression; improves memory; promotes concentration; supports the healthy functioning of the thyroid gland, the adrenal glands and the pituitary gland.

Glycine—$C_2H_5NO_2$—a nonessential amino acid. Promotes the delivery of oxygen and energy in cellular synthesis; is responsible for the strength of the immune response; stimulates the synthesis of a number of hormones.

Serine—$HOCH_2$—a nonessential amino acid. Responsible for the full assimilation of glucose by the liver and the muscles; strengthens the synthesis of humoral antibodies; participates in the synthesis of the fatty acid sheath around the nerve fibers.

Glutamic Acid—$C_5H_9NO_4$—a nonessential amino acid which is considered "brain food"; improves mental abilities; helps with fatigue; speeds up the healing of wounds; is used in the treatment of schizophrenia, alcoholism and diabetes mellitus.

Aspartic Acid—$C_4H_7NO_4$—a nonessential amino acid. Promotes the excretion of ammonia from the body, since ammonia is a highly poisonous substance for brain cells. Recent research has demonstrated that aspartic acid increases resistance to fatigue and improves endurance.

Taurine—$C_2H_7NO_3S$—a nonessential amino acid which is formed from cysteine in the liver or from methionine in other organs. It is present in milk and in some sea animals. Taurine participates in the regulation of the process of stimulation in the central nervous system; it has an antiarrhythmic effect on the cardiac muscle; it is a factor in the control of many of the biochemical reactions that take place in the process of aging; it promotes the neutralization of free radicals that appear in the cells of the body from environmental factors; it inhibits aging processes; it binds free radicals; it neutralizes toxins; it is an active participant in the restoration of epidermal tissue damaged by burns or by transplants or other surgical effects. The hair and skin contain up to 14% cystine.

Histidine—$C_6H_9N_3O_2$—a nonessential amino acid. Found in abundance in hemoglobin; widely used in the treatment of rheumatoid arthritis, allergic diseases, ulcers and anemia. A histidine deficiency is a cause of poor hearing.

Alanine—$C_3H_7NO_2$—a nonessential amino acid which is an important source of energy for muscle tissue, the brain and the central nervous system; strengthens the activity of the immune system and improves the humoral immune response; promotes the metabolism of sugar and organic acids.

Proline—$C_5H_9NO_2$—a nonessential amino acid. It is the main component of all connective tissue and is necessary for the normal functioning of the joints, tendons and ligaments; supports the working fitness of the cardiac muscle.

Ornithine—$C_5H_{12}N_2O_2$—a nonessential amino acid. It has not been isolated from proteins except after alkali hydrolysis.

We claim:

1. A method for producing an enzymatic protein hydrolysate (EPH) comprising:
    feeding raw materials into a feed processor having a multi-ton capacity;
    cutting up and mixing said raw materials in said feed processor to form a slurry;
    feeding said slurry into an alkaline-based reactor to form a hydrolysate;
    centrifuging said hydrolysate to produce an hydroxylapatite and a fish protein mix;
    acid denaturating the fish protein mix to form an acid denaturated fish protein mix;
    centrifuging the denaturated fish protein mix to produce cold fish oil and fish protein;
    alkaline denaturating and centrifuging said fish protein to produce a peptide mix and phosphoric salts of calcium;
    preserving the peptide mix with a mild acid; and
    concentrating the final product to form an EPH that primarily includes free amino acids.

2. The method of claim 1, wherein concentrating the final product includes nutrient separation and drying.

3. The method of claim 2, wherein nutrient separation is performed by a technique selected from among the group consisting of piezo-dialysis, ultrafiltration, and countercurrent extraction.

4. The method of claim 3, wherein nutrient separation results in a first product essentially consisting of free amino acids and a second product consisting of other nutrients.

5. The method of claim 1, wherein said raw materials comprise ferments and substrate from cold water marine animals.

6. The method of claim 5, wherein said marine animals are farmed fish of one species.

7. The method of claim 5, wherein said marine animals are selected from among the group consisting of cod, mackerel, and herring.

8. The method of claim 5, wherein said marine animals are pelagic fish.

9. The method of claim 5, wherein said marine animals are blue mussels.

10. The method of claim 5, wherein said marine animals are salmon.

11. The method of claim 5, wherein said marine animals are Atlantic krill.

12. The method of claim 5, wherein said marine animals are tappai.

13. The method of claim 5, wherein said marine animals are halibut.

14. The method of claim 5, wherein said ferments are derived from a single organ.

15. The method of claim 1, wherein said EPH comprises 70–90% of the free amino acids taurine, aspartine, threonine, serine, glutamic acid, praline, glycine, alanine, valine, methionine, isoleucine, leucine, tyrosine, phenylaline, oxyhedral proline, ornithine, lysine, histidine, arginine; and a 5–25% mix of cadmium, lead, mercury, arsenic, natrium, potassium, calcium, phosphorous, magnesium, iron, zinc, copper, manganese, selenium, cobalt, molybdenum, and chromium.

* * * * *